(12) United States Patent
McKay et al.

(10) Patent No.: US 12,349,951 B2
(45) Date of Patent: Jul. 8, 2025

(54) DOUBLE HELIX BONE SCREW

(71) Applicant: BFM Holdings, LLC, Austin, TX (US)

(72) Inventors: Liam Joseph Raymond McKay, Boston, MA (US); Joshua Clayton Lyon, Lakeway, TX (US); Rylan Reed, Austin, TX (US); Randall F. Dryer, Austin, TX (US); Ali Kiapour, Newton, MA (US)

(73) Assignee: BFM Holdings, LLC, Austin, TX (US)

( * ) Notice: Subject to any disclaimer, the term of this patent is extended or adjusted under 35 U.S.C. 154(b) by 407 days.

(21) Appl. No.: 17/654,479

(22) Filed: Mar. 11, 2022

(65) Prior Publication Data

US 2022/0287750 A1  Sep. 15, 2022

Related U.S. Application Data

(60) Provisional application No. 63/263,522, filed on Nov. 4, 2021, provisional application No. 63/200,517, filed on Mar. 11, 2021.

(51) Int. Cl.
*A61B 17/86* (2006.01)
*A61B 17/84* (2006.01)
*F16B 25/00* (2006.01)

(52) U.S. Cl.
CPC ........ *A61B 17/869* (2013.01); *A61B 17/8625* (2013.01); *A61B 17/846* (2013.01);
(Continued)

(58) Field of Classification Search
CPC ... A61B 17/70; A61B 17/7055; A61B 17/764; A61B 17/869; A61B 17/8625; A61B 17/863; A61B 17/864; A61B 17/866; A61B 17/8635; A61B 17/84; A61B 17/846; A61B 17/86; A61B 2017/00526; A61B 2017/30593; A61B 2017/30622; A61B 2017/3085; A61B 2017/3092;
(Continued)

(56) References Cited

U.S. PATENT DOCUMENTS 6,656,184 B1  12/2003  White et al.
7,914,532 B2   3/2011  Shaver et al.
(Continued)

FOREIGN PATENT DOCUMENTS

CN  107126281 A  *  9/2017
DE  102018005690 A1  8/2019
(Continued)

OTHER PUBLICATIONS

SpineMarketGroup, "10 Sacroiliac Joint Fusion Systems to know . . . !" [Accessed on Apr. 22, 2021 at http://thespinemarketgroup.com/10-sacroiliac-joint-fusion-systems-to-know/\.
(Continued)

*Primary Examiner* — Marcela I. Shirsat
(74) *Attorney, Agent, or Firm* — Husch Blackwell LLP

(57) ABSTRACT

A surgical screw is provided for use in fixing or fusing bone. The screw may include each of an inner and an outer helical thread that extends along its length. The geometries of the helices and the relationship between the inner thread and the outer thread may improve the performance of the screw. For example, the two helices may operate to improve the manner in which the screw can be strained.

8 Claims, 15 Drawing Sheets

(52) U.S. Cl.
CPC .......... *A61B 17/863* (2013.01); *A61B 17/8635* (2013.01); *A61B 17/864* (2013.01); *A61B 2017/8655* (2013.01); *F16B 25/0036* (2013.01); *F16B 25/0078* (2013.01); *F16B 25/0094* (2013.01)

(58) Field of Classification Search
CPC ........... A61B 2017/30985; A61B 2017/30995; A61B 2017/8655; F16B 25/00; F16B 25/0036; F16B 25/0078; F16B 25/0094
USPC ......... 606/300–321, 86 R, 60, 331; 411/411, 411/424; 623/23.5
See application file for complete search history.

(56) References Cited

U.S. PATENT DOCUMENTS

| | | | |
|---|---|---|---|
| 8,632,570 | B2 | 1/2014 | Biedermann et al. |
| 10,687,878 | B2 | 6/2020 | Fischer Lokou |
| 10,912,595 | B2 | 2/2021 | Huwais |
| 2018/0092677 | A1 | 4/2018 | Peterson et al. |
| 2018/0325570 | A1* | 11/2018 | Kuntz ................. A61B 17/869 |
| 2019/0298528 | A1 | 10/2019 | Lindsey et al. |
| 2022/0175432 | A1* | 6/2022 | Shen .................... A61B 17/869 |

FOREIGN PATENT DOCUMENTS

| | | | | |
|---|---|---|---|---|
| EP | 996385 | B1 | 1/2008 | |
| EP | 4008282 | A1 * | 6/2022 | ......... A61B 17/8645 |
| TW | 1753684 | B * | 1/2022 | |
| WO | 2015095965 | A1 | 7/2015 | |

OTHER PUBLICATIONS

Orthofix(R) "Firebird SI Fusion System" Orthofix US LLC, 4 pages. [Access on Mar. 17, 2022 at https://www.orthofix.com/ifus/firebird-si-fusion-system/].

SI-Bone(R), iFuse-3D Implant System, SI-Bone, Inc., 2 pages. [Accessed on Mar. 17, 2022 at https://si-bone.com/providers/solutions/ifuse/ifuse-3d].

* cited by examiner

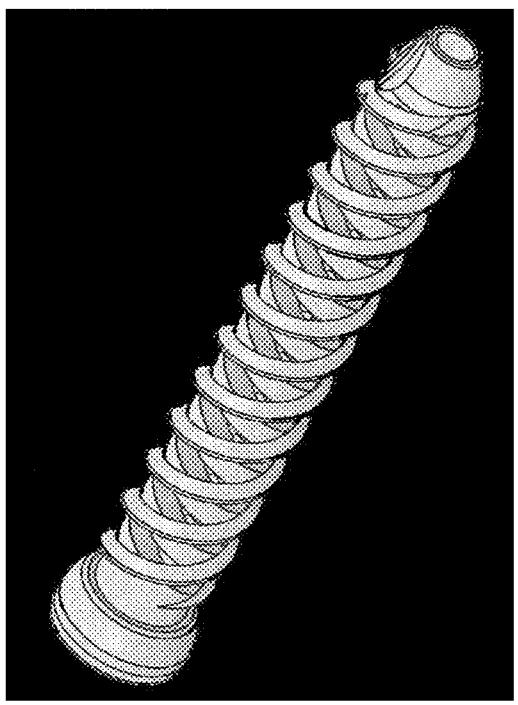
FIG. 1A
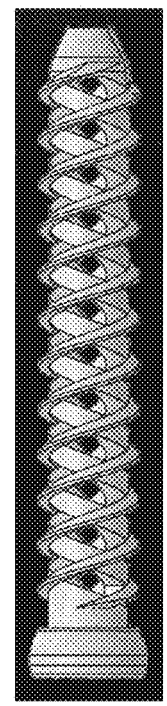
FIG. 1B
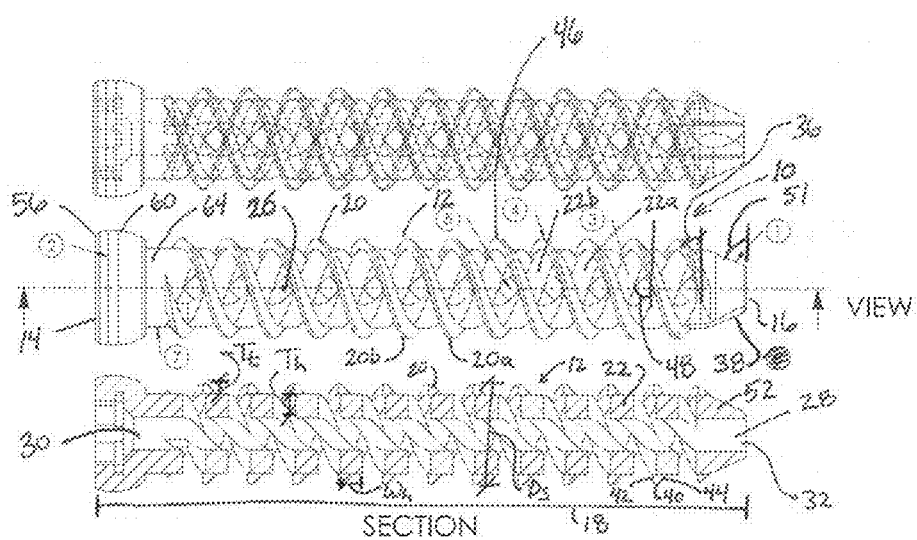
FIG. 1C
FIG. 1D
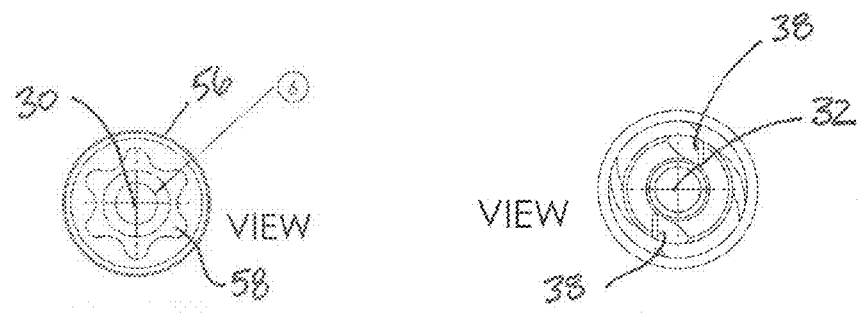
FIG. 1E
FIG. 1F

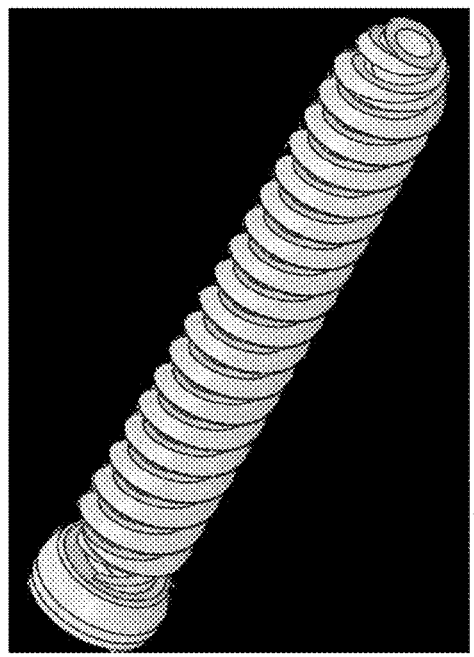
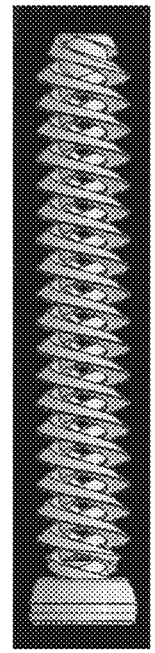
FIG. 2A  FIG. 2B
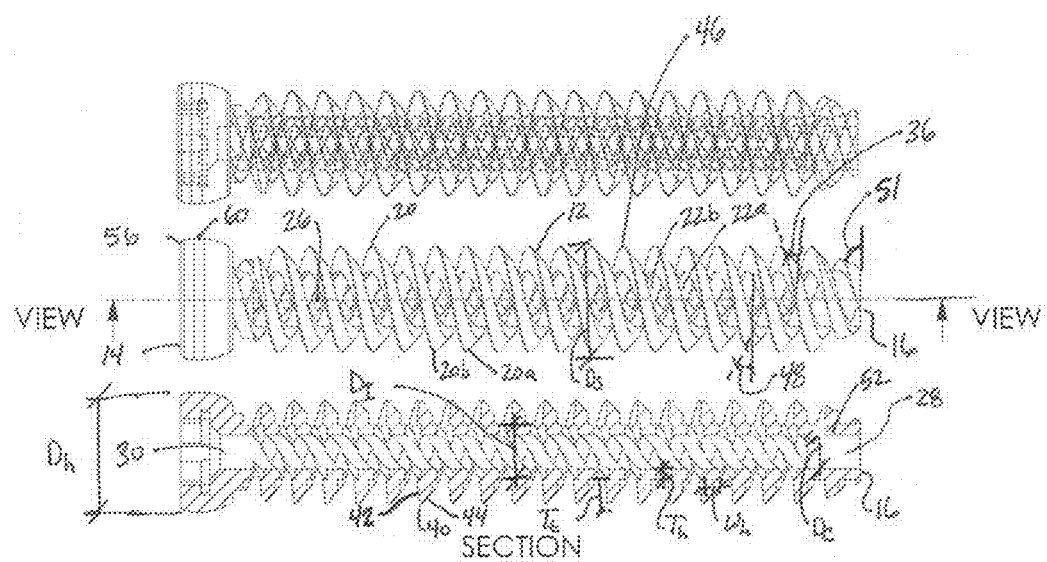
FIG. 2C
FIG. 2D
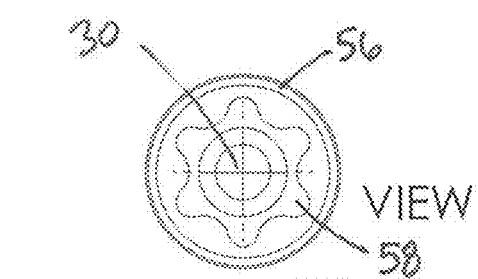
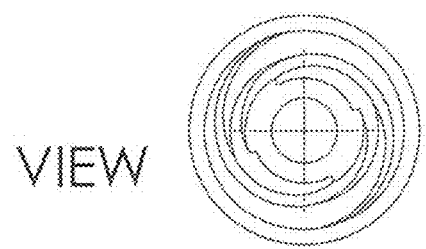
FIG. 2E  FIG. 2F

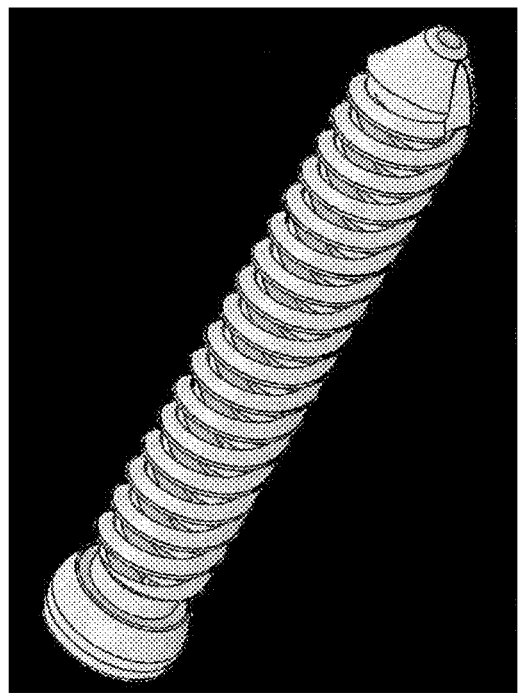
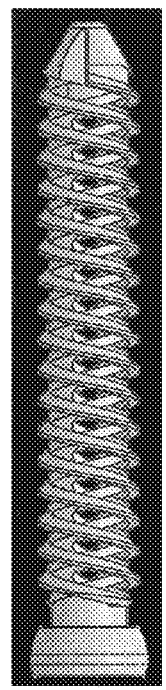
FIG. 3A  FIG. 3B
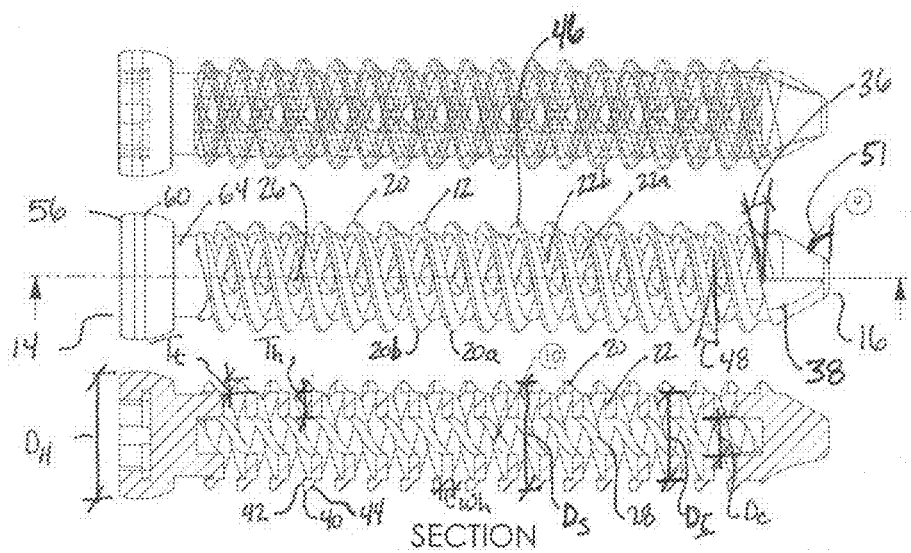
FIG. 3C
FIG. 3D
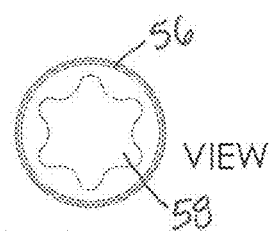
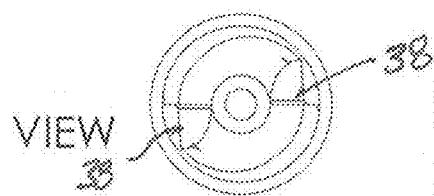
FIG. 3E  FIG. 3F

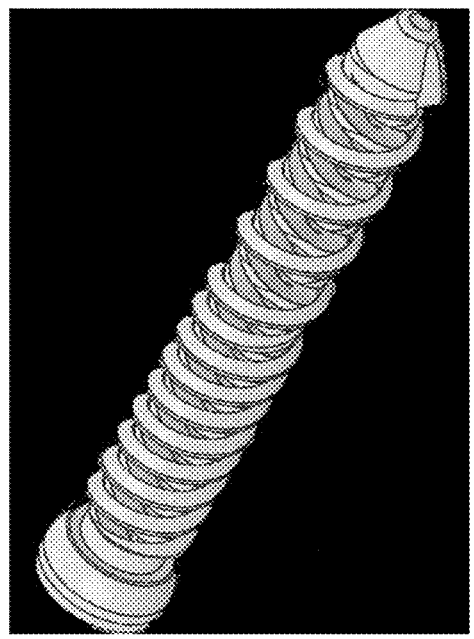
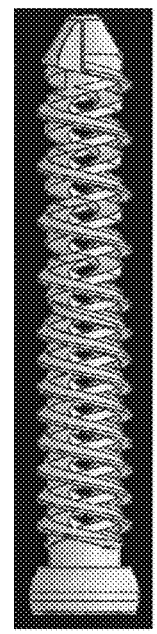
FIG. 4A          FIG. 4B
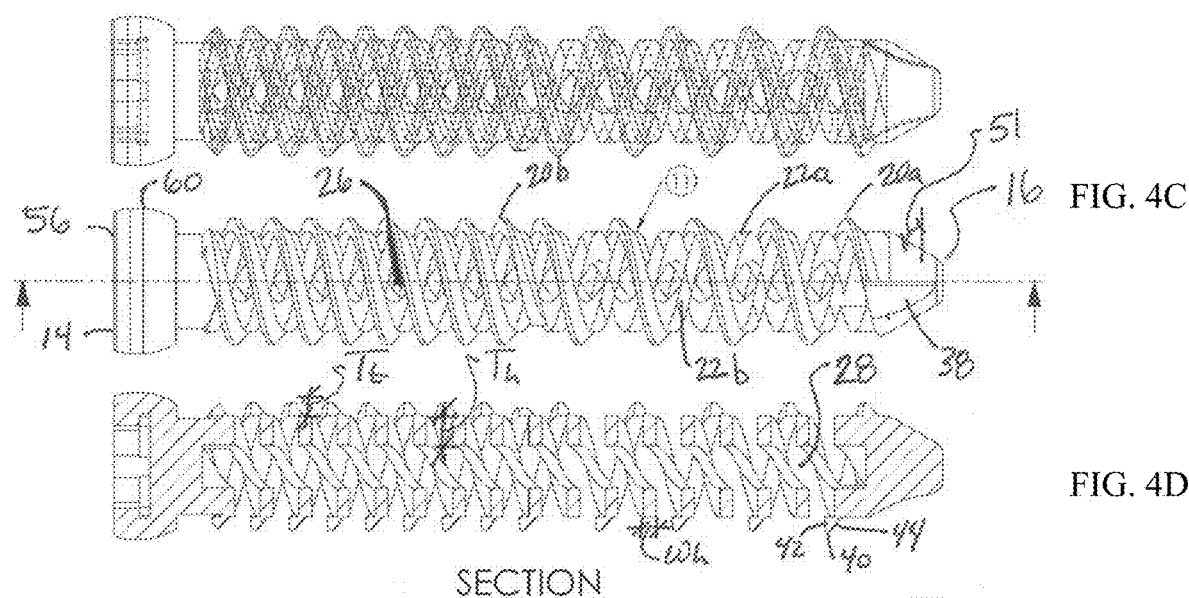
FIG. 4C
FIG. 4D
FIG. 4E          FIG. 4F

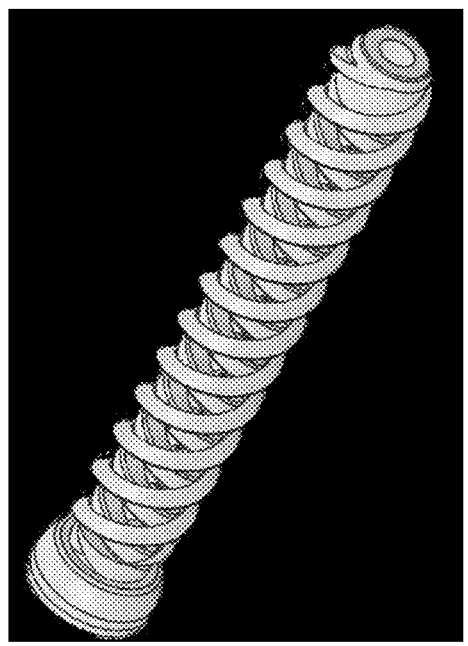
FIG. 6A
FIG. 6B
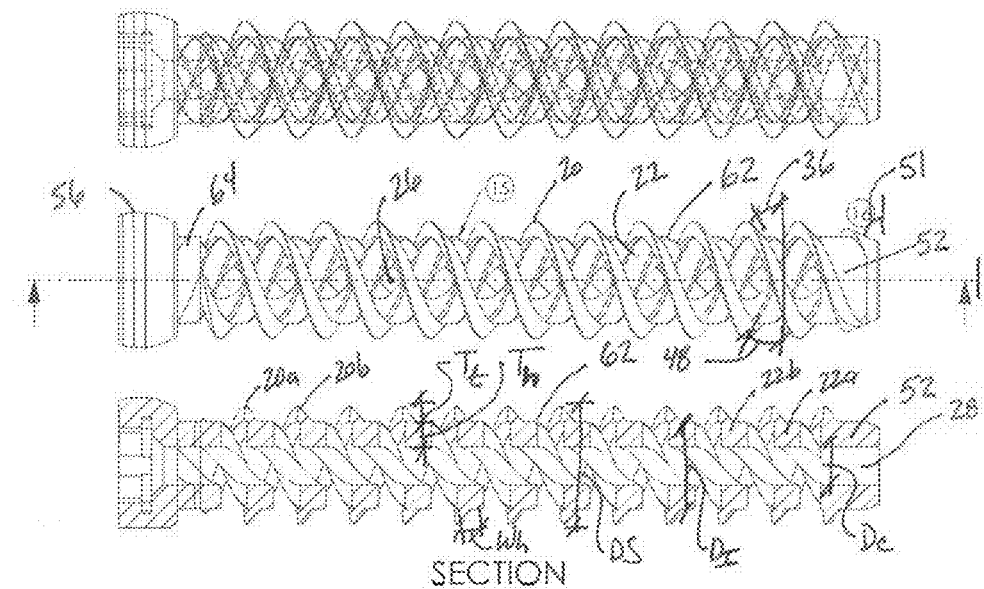
FIG. 6C
FIG. 6D
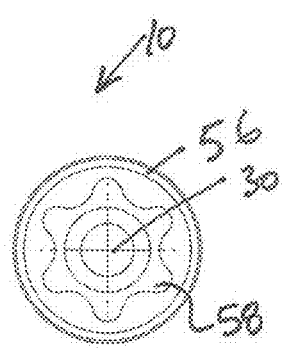
FIG. 6E
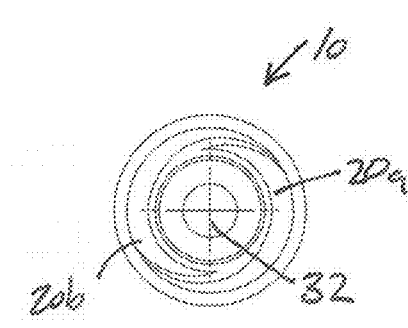
FIG. 6F

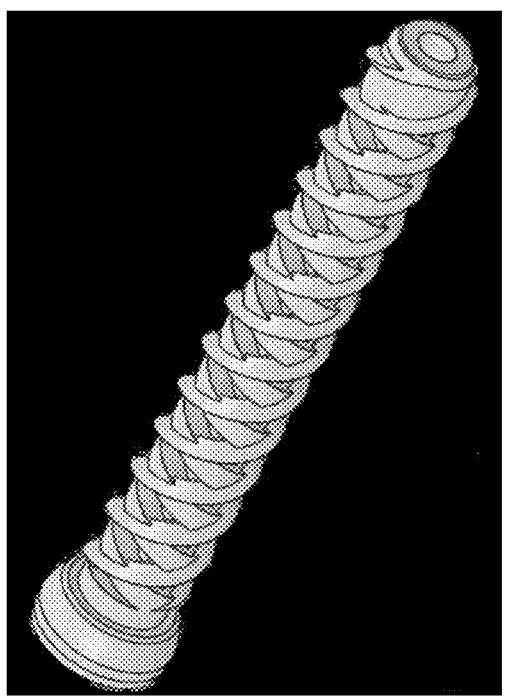
FIG. 7A
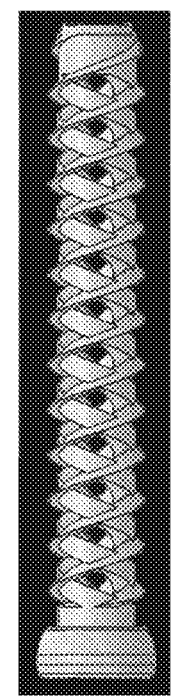
FIG. 7B
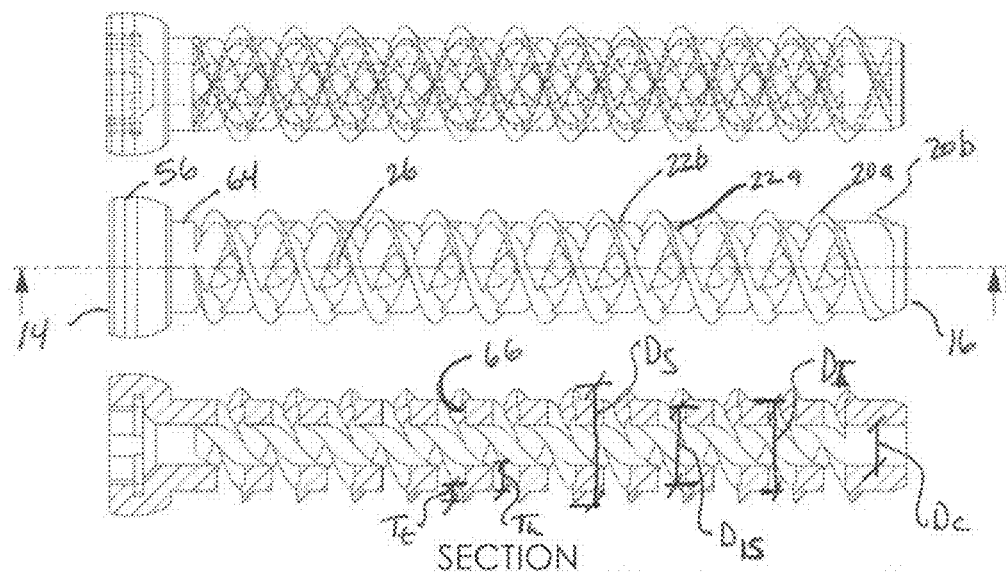
FIG. 7C
FIG. 7D
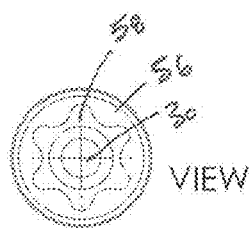
FIG. 7E
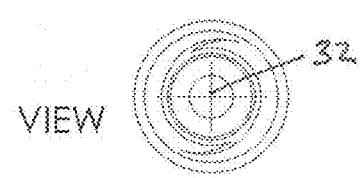
FIG. 7F

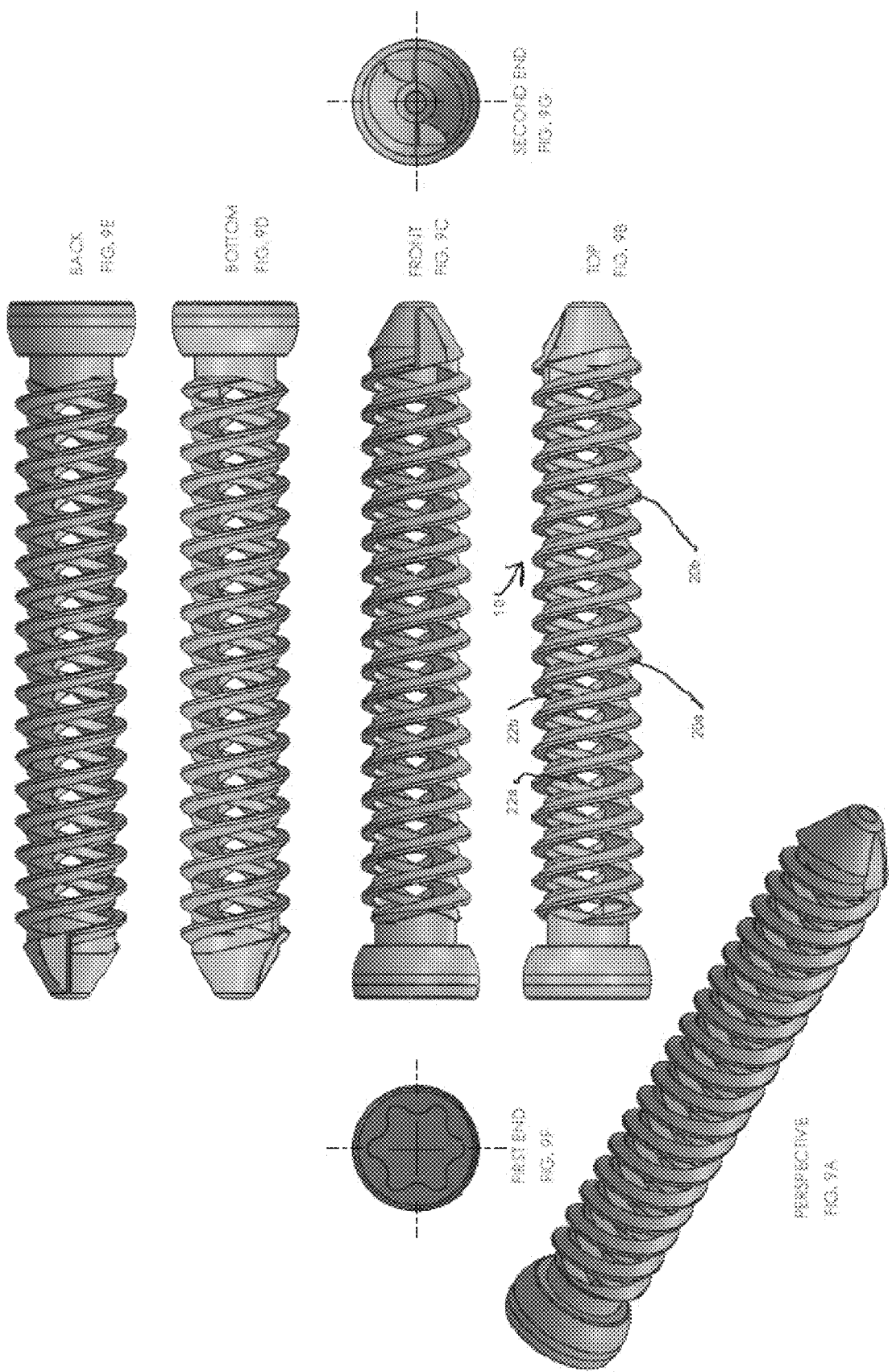

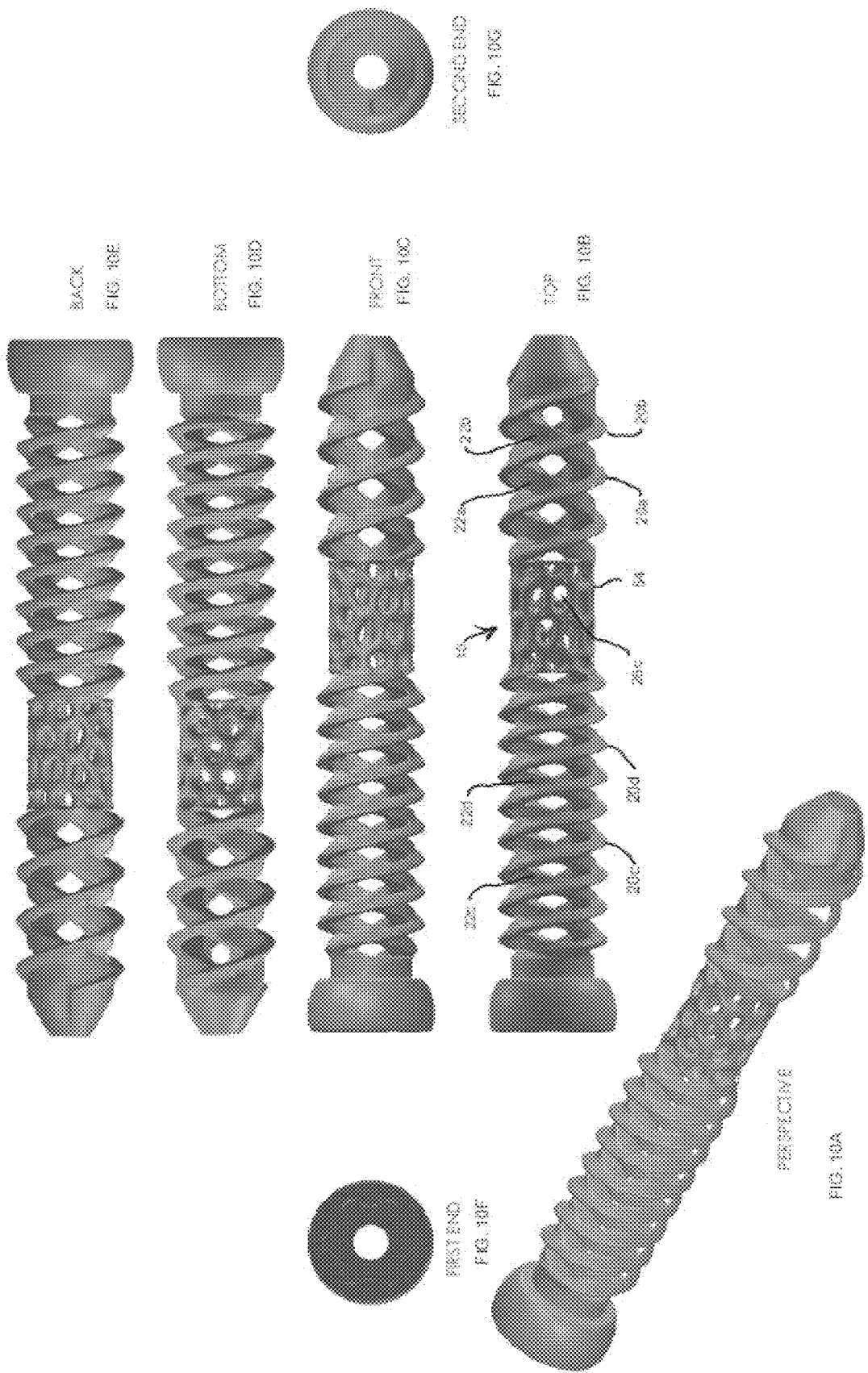

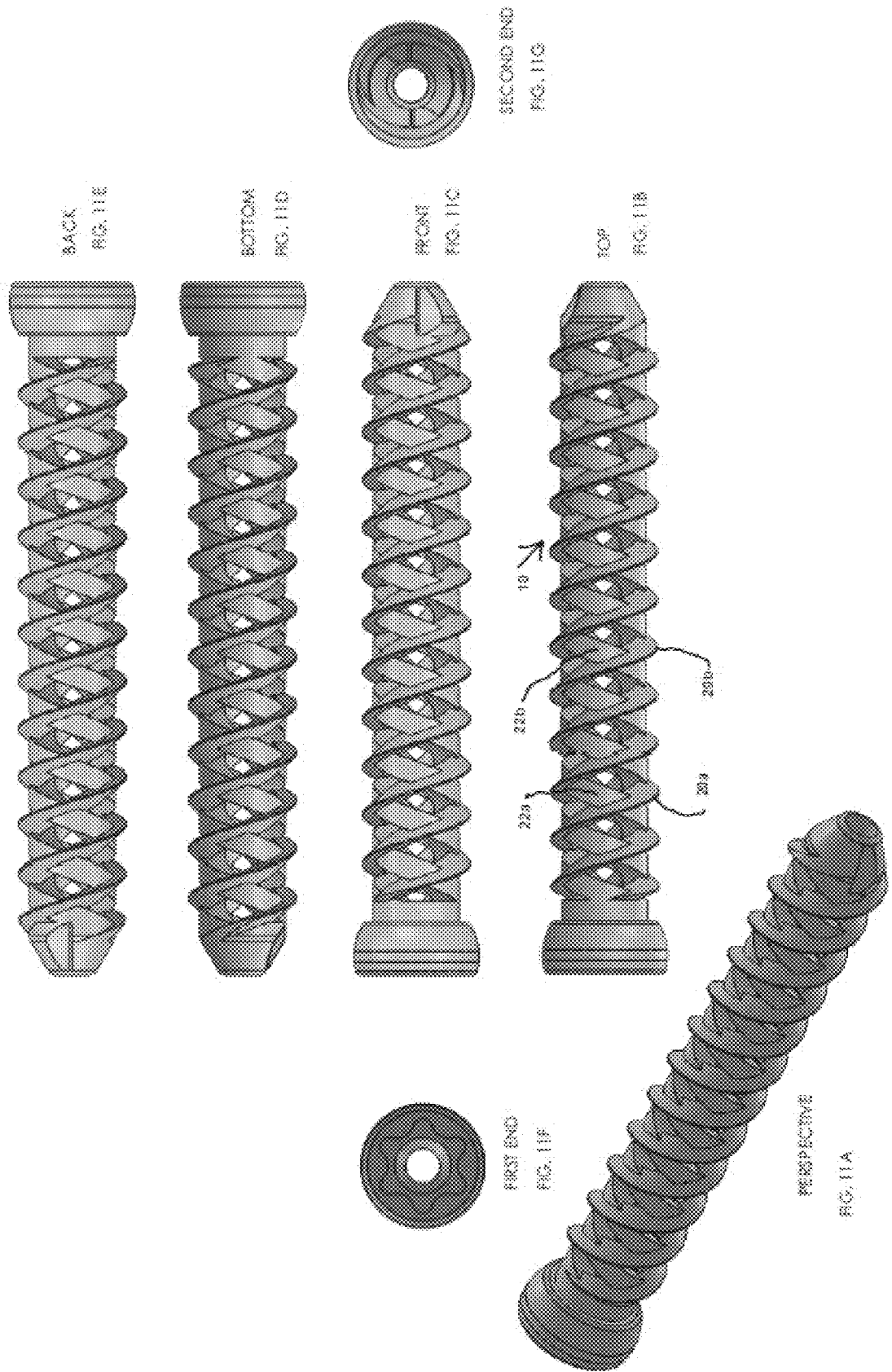

DOUBLE HELIX BONE SCREW

CROSS-REFERENCE TO RELATED APPLICATION

This application claims priority to U.S. Provisional Patent Application Ser. No. 63/200,517, filed on Mar. 11, 2021, entitled "DOUBLE HELIX BONE SCREW" and U.S. Provisional Patent Application Ser. No. 63/263,522, filed on Nov. 4, 2021, entitled "INTERSPINOUS PROCESS FIXATION DEVICE" both of which are currently pending, and the entire disclosures of which are incorporated herein by reference.

FIELD OF THE INVENTION

This present invention relates to a bone screw with improved flexural and bone grafting functionalities.

BACKGROUND OF THE INVENTION

There are many types of hardware for the fixation or fusion of bones. The majority of current bone fixation implants are solid-bodied, often with numerous cavities for increased bone growth through the implant and shorter fixation times. This leads to an implant which strains slightly in response to lateral forces, however, such existing designs are very stiff in compression along the implant body. Solely having slot style cavities in a solid body implant limits strains in response to all non-lateral forces experienced by an installed implant. In particular, the implants are incredibly stiff under compression at the tip and head, thus minimizing the promotion of bone growth due to strains in the hardware.

Further, the solid body of the implant limits bone throughgrowth solely to the designed cavities. These existing slot style cavities through the solid body must be small enough to maintain the strength of the implant, which also limits the volume of bone graft which can be packed into it, if the surgeon elects to do so prior to implantation. Current hardware often takes the form of threaded screws which are drilled into the bone, or elongated rods with a plurality of faces which are impacted into the bone. Standard machining of titanium surgical screws leaves the surface of the screws very smooth. This limits potential for bone on-growth on the surface. Threadless implants can have low pullout strength compared to threaded screw implants.

One existing system uses metal 3D printing to create a roughened surface triangular body implant for sacroiliac joint fixation. The implant does not include any threads, which contributes to a very weak pullout strength of the implant. Although there are fenestrations along the body of the implant to allow for bone through growth into the center cannula, the triangular design limits the amount of lateral contiguous bone growth through the implant.

Another existing titanium 3D printed surgical screw has slot style fenestrations which only provide the opportunity for lateral contiguous bone growth in two plane views. The construction of this screw does not allow for any additional bone graft volume packing over an even more conventional machined surgical screw.

There is minimal strain in both of these implants under compression. Thus, neither of these implants improve the potential for bone-growth promoted by strain in the implant.

As such, there is a need in the art for an improved bone screw which has some flexural capacity in compression, and improves bone grafting, anchorage, and bone growth when installed.

SUMMARY OF THE INVENTION

The invention hereof provides an improved bone screw having various properties that increase its ability to strain without affecting its strength. The various embodiments disclosed in the invention may include an inner and an outer helix, and various relationships between the thicknesses and angles of those helices may operate to alter the qualities of the screw. That way, the screw may be tuned and customized for a particular use.

BRIEF DESCRIPTION OF THE SEVERAL VIEWS OF THE DRAWINGS

The accompanying drawings form a part of the specification and are to be read in conjunction therewith, in which like reference numerals are employed to indicate like or similar parts in the various views:

FIGS. 1A-1F are multiple views of one embodiment of a bone screw in accordance with the teachings of the present disclosure;

FIGS. 2A-2F are multiple views of one embodiment of a bone screw in accordance with the teachings of the present disclosure, wherein the inner framework helix accounts for approximately 50% of the screw diameter;

FIGS. 3A-3F are multiple views of one embodiment of a bone screw in accordance with the teachings of the present disclosure having a solid tip for surgical applications where a guide wire or pin is not necessary;

FIGS. 4A-4F are multiple views of one embodiment of a bone screw in accordance with the teachings of the present disclosure, wherein the outer thread helix begins as a single lead thread;

FIGS. 6A-6F are multiple views of one embodiment of a bone screw in accordance with the teachings of the present disclosure having with rounded edges on the inner body helix;

FIGS. 7A-7F are multiple views of one embodiment of a bone screw in accordance with the teachings of the present disclosure;

FIGS. 9A-9G are a perspective, front, back, top, bottom and end views of a bone screw in accordance with the teachings of the present disclosure;

FIGS. 10A-10G are a perspective, front, back, top, bottom and end views of a bone screw in accordance with the teachings of the present disclosure;

FIGS. 11A-11G are a perspective, front, back, top, bottom and end views of a bone screw in accordance with the teachings of the present disclosure.

DETAILED DESCRIPTION OF THE INVENTION

Figure 5A:
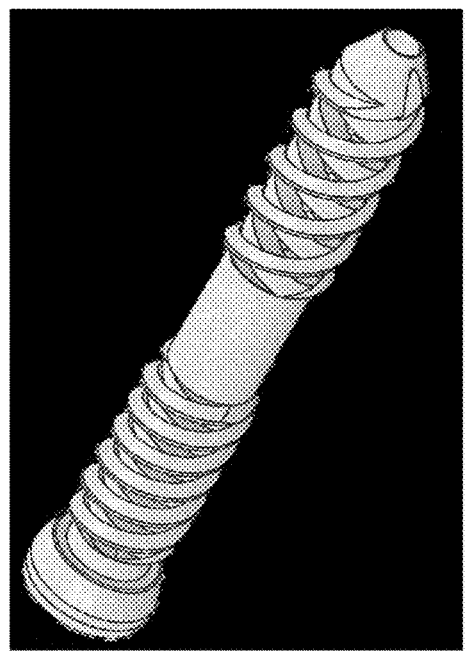
FIGS. 5A-5E are multiple views of one embodiment of a bone screw in accordance with the teachings of the present disclosure including a transitional barrel/reduced diameter portion that also forms a transition from a steeper thread pitch/angle to a lower thread pitch/angle.
Figure 5B:
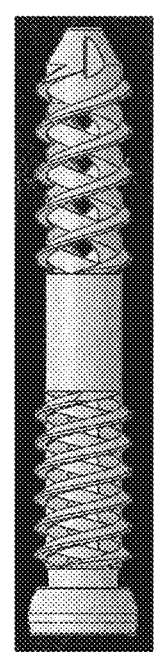
Figure 5C:
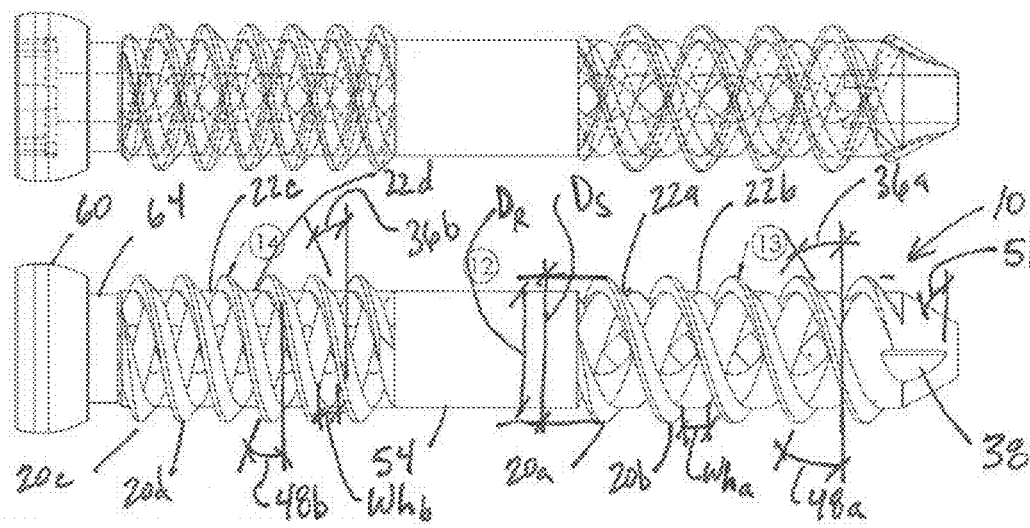
Figure 5D:
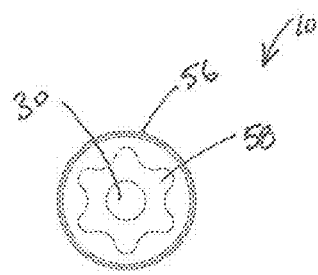
Figure 5E:
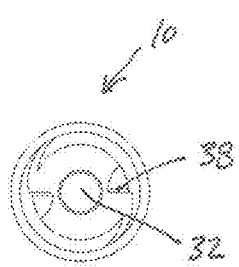
Figure 8A:
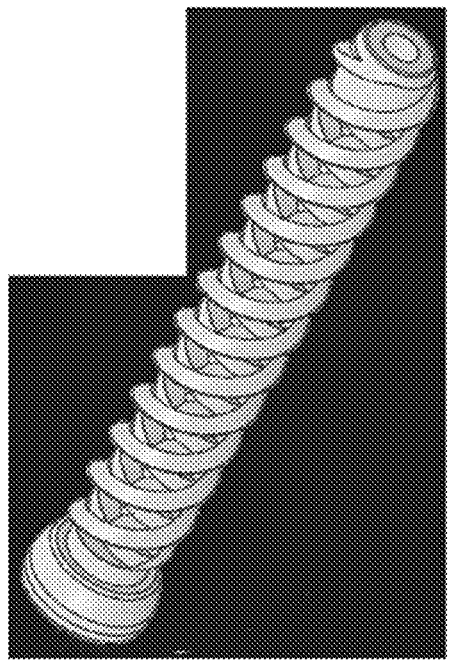
FIGS. 8A-8F are multiple views of one embodiment of a bone screw in accordance with the teachings of the present disclosure.
Figure 8B:
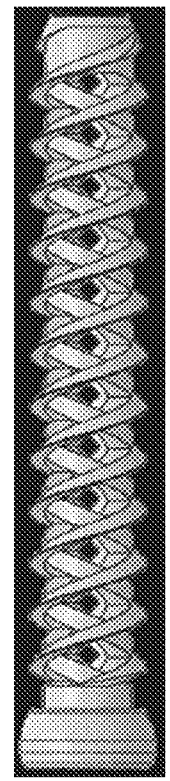
Figure 8C:
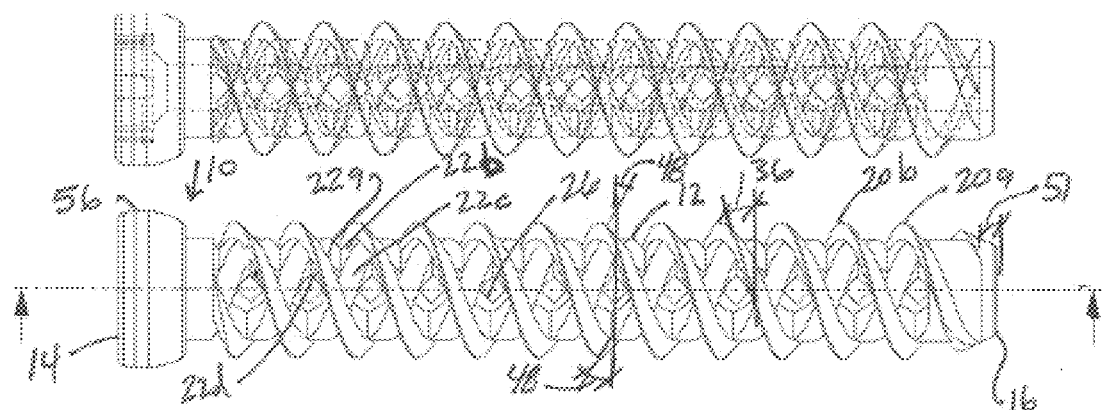
Figure 8D:
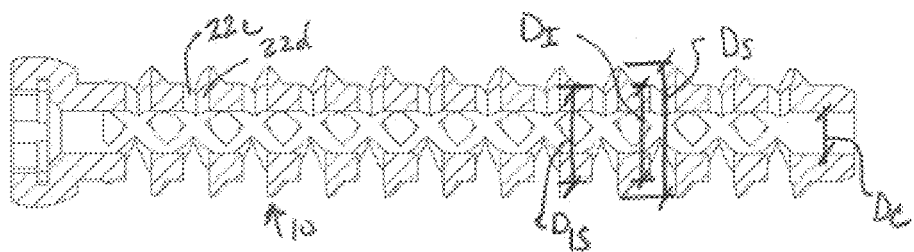
Figure 8E:
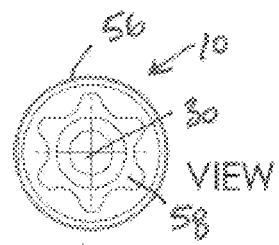
Figure 8F:
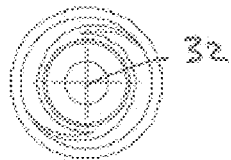
Figure 12:
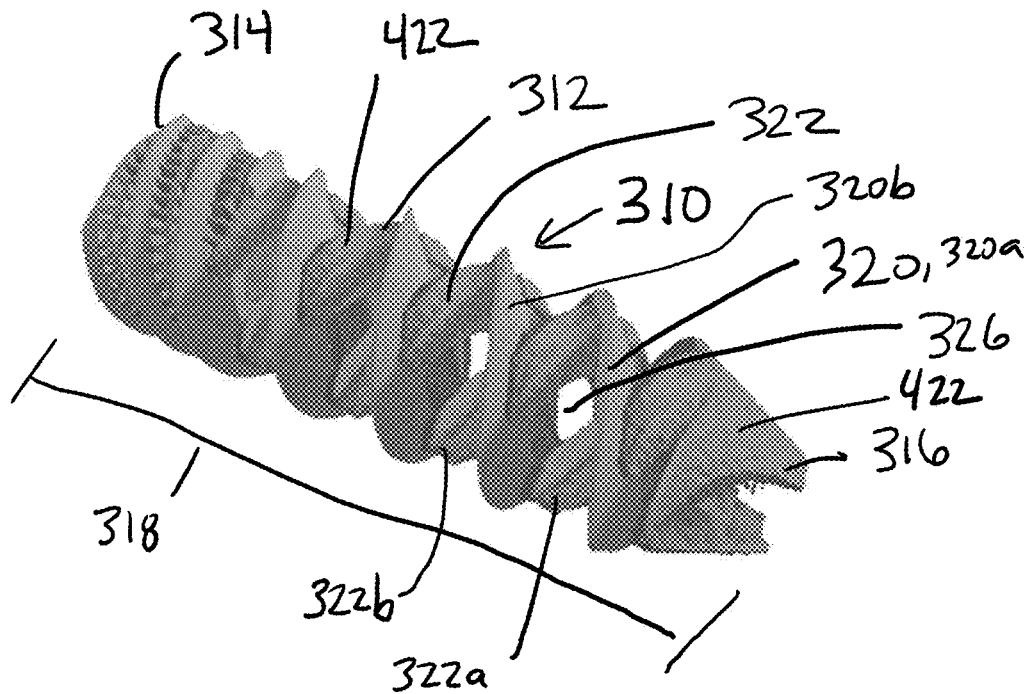
FIGS. 12-18 are perspective, front, back, top, bottom, first end and second end views of one embodiment of a doublehelix screw in accordance with the teachings of the present disclosure.

The following detailed description of the present invention references the accompanying drawing figures that illustrate specific embodiments in which the invention can be practiced. The embodiments are intended to describe aspects of the present invention in sufficient detail to enable those skilled in the art to practice the invention. Other embodiments can be utilized and changes can be made without departing from the spirit and scope of the present invention. The present invention is defined by the appended claims and, therefore, the description is not to be taken in a limiting sense and shall not limit the scope of equivalents to which such claims are entitled.

The present invention is directed toward a double helix bone screw. Description of the illustrated embodiments: References to drawings of the embodiments will now be made. No limitation of the scope of the claims or further modifications of the device is intended by the illustrated embodiments.

FIG. 1 shows one embodiment of a bone screw 10 comprising a body 12, a drive end 14 and a leading end 16. The drive end 14 and leading end 16 define a length 18. Bone screw 10 may also include threads 20, wherein certain embodiments may include one thread, or two threads 20 disposed in a double helix relationship as shown in FIG. 1. Bone screw 10 also includes an inner framework helix 22. Like the threads 20, the inner framework helix 22 may be one element or two elements disposed in a double helix relationship. Both the threads 20 and the framework helix 22 may be any number of individual threads or members, but they preferably include two threads offset 180 degrees on the circumference of the screw.

The inner framework helix 22 is generally orientated in an opposite direction of rotation of the threads 20. In this configuration, a first inner framework helix 22a and a second inner framework helix 22b are arranged in a parallel relationship and both intersect a first thread 20a and a second thread 20b, which are also arranged in a parallel relationship, at several intersection joints 24. The first inner framework helix 22a, second inner framework helix 22b, first thread 20a and second thread 20b also define openings 26. Inner framework helix 22 may have any cross-sectional shape, such as rectangular or conical. In one embodiment, inner framework helix 22 has a rectangular shape with at helix thickness of Th and a helix width of Wh. However, inner framework helix 22 member may be circular or oval or any other cross-sectional shape providing the desired stiffness and flexure.

Generally, inner framework helix 22 defines a cannula 28 through the entire length of the screw 10. The cannula 28 includes a driven end opening 30 and a leading end 32 opening that defines a length Lc, and a cannula diameter 34. In other embodiments, cannula 28 may be present solely within a portion of the inner framework helix 22 with solid ends. This embodiment allows flexure in the axial direction in compression or tension, but it provides solid ends for rigidity when guides and/or a through-cannula is not required.

In one embodiment, threads 20 are orientated at a thread angle 36 and the leading end 16 of screw 10 may include a cutting edge 38 as known in self-drilling screws. The threads 20 may comprise a thread edge 40 defined by the intersection of a first thread surface 42 and a second thread surface 44. In one embodiment, the threads 20 may have a wedge shape 46. In one embodiment, the threads 20 are arranged such that, when looking down from the driven end, the threads 20 travel downward in a clockwise direction of rotation at the thread angle 36. In one embodiment, the thread angle 36 is about 6 degrees and can range to 12 degrees in other versions or sections of the screw 10. However, additional ranges between 2-45 degrees are within the scope of the present invention.

In one embodiment, the inner framework helix 22 is arranged such that, when looking down from the driven end, the inner framework helix 22 travels downward in a counter-clockwise direction of rotation at a helix angle 48. In one embodiment, the helix angle 48 is about 6 degrees and can range to 12 degrees in other versions or sections of the screw 10. However, additional ranges between 2-45 degrees are within the scope of the present invention. In one embodiment, the helix angle 48 and the thread angle 36 are equal, but in other embodiments, the angles 36 and 48 may be different from one another. One purpose of matching or having different angles 36 and 48 is to create a balanced spring-like construction to provide flexure in an axial compression direction of the screw 10 and so the angles may be adjusted based upon the thickness of the threads 20 and inner framework helix 22 members accordingly.

The leading end 16 may have a number of different configurations. As shown in FIG. 1, leading end 16 may have a leading edge taper 50 at a taper angle 51. As shown, taper angle may vary which may affect the length of the tapered portion of the leading end 16. As further shown in FIG. 1, leading end 16 may include a solid body portion 52 extending a length Lp from the end 16 toward the driven end 14. This solid body portion 52 provides rigidity and strength when introducing the screw 10 and where the screw 10 first engages the bone.

As shown in FIG. 5, the screw 10 may include a body 12 having a reduced diameter portion 54, wherein the reduced diameter portion 54 may be comprised of a solid cylindrical portion having a solid sidewall. The reduced diameter portion 54 may be a transition between sections of screw 10 having different thread angles 36 and helix angles 48.

As illustrated, the driven end 14 of screw 12 includes a head 56 which has a driver receptacle 58 disposed therein. The driver receptable 58 can be arranged to correspond with any current or future industry utilized driver head. In one embodiment, the drive receptacle is configured to receive a Torx driver head. However, any known driver, such as square, Phillips, hex, slot, or any other driver now known or hereafter developed can be utilized. Further, the head 56 may include a tapered sidewall 60 as shown, but the sidewall 60 could be of any profile. Further, one embodiment of screw 10 includes a neck portion 64 or transition disposed between the head 56 and the threads 20 and inner framework helix 22. Neck portion 64 may have a solid sidewall forming a cylinder around cannula 28, or alternatively, may have a solid cross-section.

FIG. 1 illustrates one embodiment including dual threads 20a and 20b, where thickness of the thread Tt extends for about 20% of the overall screw 10 diameter Ds. The interaction between the two opposing helices formed between the threads 20 and the inner framework helix 22 creates openings 26 for contiguous bone growth through the implant 10. In this embodiment, the shaft is hollow and has a longitudinal cannula 28 extending through the entire screw. The cannula 28 may have a constant diameter or may widen in diameter at the shaft. In this embodiment, there is a solid 2 mm transition body 64 which connects the helical body 12 to the screw head 56. In some embodiments, at the leading tip 50, there are two cutting flutes 38 that allow for ease of threading and self-drilling through the bone.

FIG. 2 is a bone screw 10 with the inner framework helix 22 diameter Di accounting for approximately 50% of the screw diameter Ds. In some embodiments, the threads 20 will be the opposite helix, and thread Tt extends for about 20% of the overall screw 10 diameter Ds with the center body cannula 28 diameter 34 or Dc comprising the remainder of Ds.

FIG. 3 illustrates a bone screw 10 with a solid leading end 16 which may be more beneficial in certain surgical applications where a guide wire or pin is not necessary. In some embodiments, the cannula 28 occupies most of the body despite not passing through the tip or head 56 to retain the spring-like construction of the body 12 and flexure in the axial compression direction. In some embodiments, the screw 10 is cannulated in the entire length as described above for ease of placement down a Steinmann pin or k-wire during surgery. The diameter of cannula 28 may be sized in accordance with each of these guide methods.

FIG. 4 illustrates an embodiment of bone screw 10 wherein bone screw 10 includes the thread 20 beginning as a single lead thread 20a. In some embodiments, halfway along the length 18 of the screw from the leading end 16, the outer helical thread 20b becomes a double lead thread including both thread 20a and thread 20b. In other embodiments (not shown), a single thread 20a may continue as the only thread along the length 18 of screw 10.

FIG. 5 illustrates an embodiment of bone screw 10 having a reduced diameter portion 54 of solid sidewall, or a barrel section, which provides additional stiffness and may be a transition from a steeper thread pitch/angle 36a at the leading end to a lower thread pitch/angle 36b at the driven end. In addition, the embodiment in FIG. 5 may include the inner framework helix 22 being orientated at a first helix angle 48a at the leading end and a second helix angle 48b at the driven end. Moreover, the size and shape of the cross-section of threads 22c and 22d may differ from that of 22a and 22b, in both the thickness and/or width. In an alternative embodiment, the reduced diameter portion 54 may be an open lattice structure similar to the inner framework helix, but in both directions of rotation, for bone graft packing and bone through growth. In some embodiments, the thread pitches/angles 36 and 48 of the leading and driven threaded sections may be the same.

In addition to the other features described above, FIG. 6 is a bone screw 10 with rounded edges 62 on the inner helix 15. In some embodiments there are smooth fillet transitions (not shown) between the inner framework helix 22 and the threads 20. In some embodiments (not shown) the screw has a non-tapered leading end 16, or a very short tapered section like that shown in FIG. 6.

FIG. 7 shows an embodiment of bone screw 10 in which the inner diameter Dis of the threads 20 is smaller than the outer diameter Di of the inner framework helix 22. This creates an overlap of volume between the two helices where they overlap as shown.

FIG. 8 shows an embodiment of bone screw 10 in which the inner diameter Dis of the threads 20 is equal to the outer diameter Di of the inner framework helix 22. This creates a configuration wherein the entire thickness of the threads extends outward from the inner framework helix 22 as shown.

In some embodiments, the dual helix bone screw 10 is additively manufactured in Grade V titanium using selective laser melting. This creates a roughened surface for increased bone purchase and on growth. The Double Helix Screw provides opportunity for bone through-growth in all directional planes due to the openings 26 formed in the double helix construction. Bone growth can easily proliferate through the screw body 12 in any direction, thus creating a more distributed fusion and is not limited to one plane like those of a solid screw body. This construction also allows for a greater volume of bone graft to be packed into the screw 10. The rigidity of current screws under tip compression is no longer an issue in the Double Helix screw because the inner framework helix 22 rotated in the opposite direction of the outer thread 20 helix creates a spring-like construction and allows for strain upon compression. In other embodiments, the screw can be made using PEEK (polyethylethylketone) plastic, nitinol metal or carbon fiber embedded additive manufacturing methods.

An alternative design configuration of screw 10 can be used as joint stabilizer and bone growth stimulator by developing macrostrain across the surface of the implant when exposed to the anatomical load. In this design configuration the screw 10 contains a semi-elastic region around the area of the screw shaft which is in-between the sacroiliac gap. The screw thread 20 at the medial and driven areas of the screw also have a slightly different pitch/angle creating a small lag in displacement as the screw advances into the bone; the lag allows the elastic portion of the screw to be stretched and develop a small pre-compression load across the threads 20. This pre-compression can magnify the macrostrain at the bone-implant interface and, in one embodiment may potentially improve the new bone growth rate and fusion rate.

The screw 10 has threads 20 which contribute to a strong pullout strength immediately following surgery. The screw 10 allows for contiguous bone growth from many different lateral and orthographic plane views due to the two helixes (threads 20 and inner framework helix 22) in reverse rotational direction which make up the main screw body 12. In taking advantage of metal 3D printing manufacturing methods, the very open screw body 12 with openings 26 as configured herein can be packed with a larger volume of bone graft than implants of the same diameter and length mentioned above. At a 65 mm implant length and assuming the screw inner body 12 (threads 20 and inner frame helix 22) accounts for 80% of the screw diameter, the screw allows for approximately a 4:3 ratio of screw material volume to bone graft volume. This assumes it is packed to the minor thread diameter Dis. The dual helix construction creates a spring like response under compression and eliminates the unnecessary stiffness in that direction which is present in the other inventions. The design of some embodiments allows for creation of a pre-compressive load across the shaft of the screw which can turn into micro-strain at the bone implant interface. According to Wolff's law, this microstrain can promote the bone growth and increase the osteogenic cell differentiation rate. The elastic properties of the screw can be customized and programmed through the design based on patient's native bone density and stiffness (osteoporotic versus normal). Thus, through the additive manufacturing process, the screw can be manufactured specifically for individual patients, which allows for maximum micro-strain generation while minimizing the risk of screw pull out by adjusting the screw pre-compression load based on patient's anatomy.

In one embodiment, the helical screw incorporates dual-lead threads 20a and 20b at a 6-degree pitch/angle. These threads 20 make up the outer diameter Ds of the screw of 10.1 mm. The outer helical threads 20 form an auger-like shape. The outer threads 20 run to the outer surface of the inner framework helix 22 which has a diameter Di of 5.3 mm. The inner framework helix 22 incorporates a 6-degree pitch/angle double helix design as well, but in the opposite direction of rotation. The inner framework helix 22 thickness is 1 mm, creating a 3.3 mm diameter Dc of cannula 28 through the length of the screw. The leading tip of the screw has a 25-degree tapered tip which begins 3 mm from the centerline. The head 56 of the screw has a T50 Torx drive and a chamfered opening 30 for cannula 28 access.

In some embodiments, the thread pitch/angle 36 and 48 is about 6 degrees and can range to 12 degrees in other versions. However, additional ranges between 2-45 degrees are within the scope of the present invention.

FIGS. 9A-9G are a perspective, front, back, top, bottom and end views of a bone screw in accordance with the teachings of the present disclosure. In this embodiment, a double helix thread 20a and 20b, and a double helix inner framework helix 22a and 22b consistent with previous labels shown. In this embodiment, there is no opening at the leading end of the cannula 28.

FIGS. 10A-10G are a perspective, front, back, top, bottom and end views of a bone screw in accordance with the teachings of the present disclosure. In this embodiment, a double helix thread 20a and 20b, and a double helix inner framework helix 22a and 22b consistent with previous labels shown. In this embodiment, a reduced diameter portion 54 transitions from a steeper thread pitch/angle 36a at the leading end to a lower thread pitch/angle 36b at the driven end. Further, the inner framework helix 22 is oriented at a first helix angle 48a at the leading end and a second helix angle 48b at the driven end. Moreover, the size and shape of the cross-section of helix members 22c and 22d differ from that of 22a and 22b, in both the thickness and/or width with the leading end having thicker threads and body portion. In addition, the reduced diameter portion 54 sidewall an open lattice structure having openings 26c for bone graft packing and bone through growth.

FIGS. 11A-11G are a perspective, front, back, top, bottom and end views of a bone screw in accordance with the teachings of the present disclosure. In this embodiment, a double helix thread 20a and 20b, and a double helix inner framework helix 22a and 22b consistent with previous labels shown. Further, this embodiment of bone screw 10 includes the inner diameter Dis of the threads 20 is smaller than the outer diameter Di of the inner framework helix 22. This creates an overlap of volume between the two helices where they overlap as shown. (See detailed description of FIG. 5 above).

FIGS. 12-18 shows one embodiment of a bone screw 310 comprising a body 312, a drive end 314 and a leading end 316, the drive end 314 and leading end 316 defining a length 318. Bone screw 310 may also include threads 320, wherein certain embodiments may include one thread, or two threads 320 disposed in a double helix relationship as provided in FIG. 12. Bone screw 310 also includes an inner framework helix 322. Similar to the threads 320, the inner framework helix 322 may be one element or two elements disposed in a double helix relationship. Both the threads 320 and the framework helix 322 may be any number of individual threads or members but will preferably include two threads offset 180 degrees on the circumference of the screw.

The inner framework helix 322 is generally oriented in an opposite direction of rotation of the threads 320. The direction of rotation may also be described either as a "right hand" helix and a "left hand" helix. In this configuration, a first inner framework helix 322a and a second inner framework helix 322b are arranged in a parallel relationship and both intersect a first thread 320a and a second thread 320b, which are also arranged in a parallel relationship, at several intersection joints 324. The first inner framework helix 322a, second inner framework helix 322b, first thread 320a and second thread 320b also define openings 326. Inner framework helix 322 may have any cross-sectional shape, such as rectangular or conical. In one embodiment, inner framework helix 22 has a rectangular shape. However, inner framework helix 22 member may be circular or oval or any other cross-sectional shape providing the desired stiffness and flexure.

Figure 17:
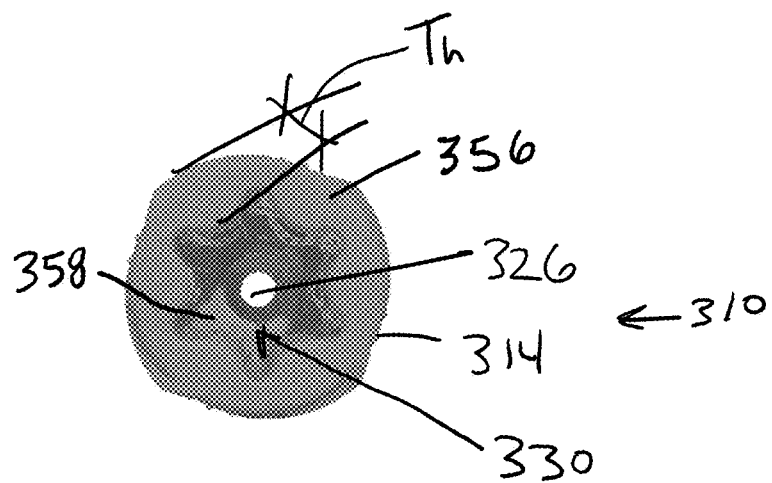
Figure 18:
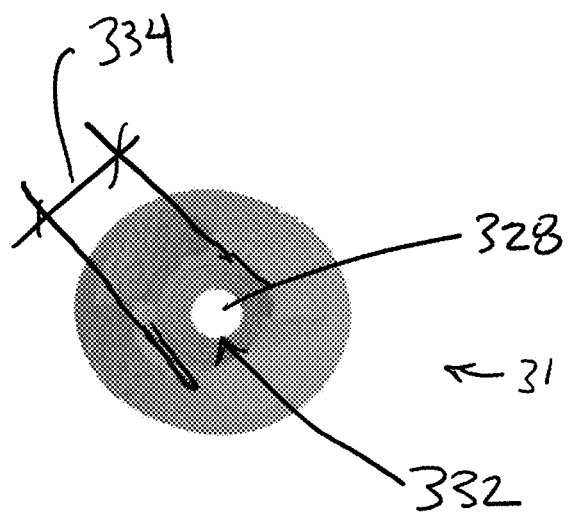

In one embodiment, as best shown in FIGS. 17 and 18, inner framework helix 322 defines a cannula 328 through the entire length 318 of the screw 310. The cannula 328 includes a driven end opening 330 and a leading end 332 opening that defines a length Lc, and a cannula diameter 334. In other embodiments, cannula 328 may be present solely within a portion of the inner framework helix 322 with solid ends. This embodiment allows flexure in the axial direction in compression or tension, but it also provides solid ends for rigidity when guides and/or a through-cannula is not required.

As shown in FIGS. 12-18, the driven end 314 of screw 312 includes a head 356 which has a driver receptacle 358 disposed therein. In this embodiment, however, head 356 does not differ in diameter from the remainder in the screw and the threads may extent to the driven end 314. This construction is sometimes referenced in the industry as "headless." The head 356 may also include a porous construction wherein the pores are configured throughout the entire head. The pores 420 may be radially oriented, or there may be a perforated outer wall 410 having a thickness "Th" surrounding the cannula 328. The perforations may also be considered an open lattice structure as described above. Threads 320 may sit on top of or be integral with this perforated head wall 412. As shown in FIG. 17, a desired drive receptacle 358 may be formed in the head 356. The drive receptacle 358, in one embodiment, is configured to receive a Torx driver head. However, any known driver, such as square, Phillips, hex, slot, or any other driver now known or hereafter developed can be utilized.

Figure 13:
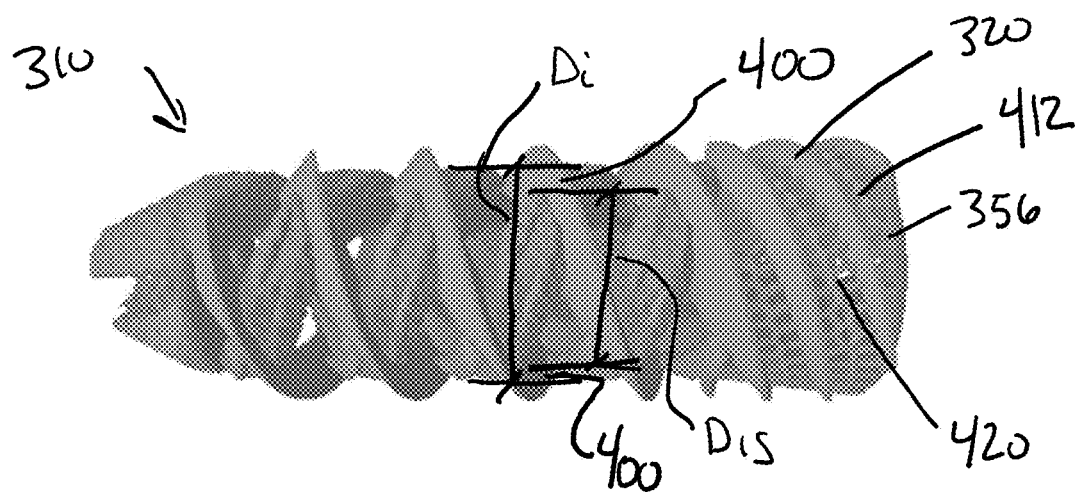
Figure 14:
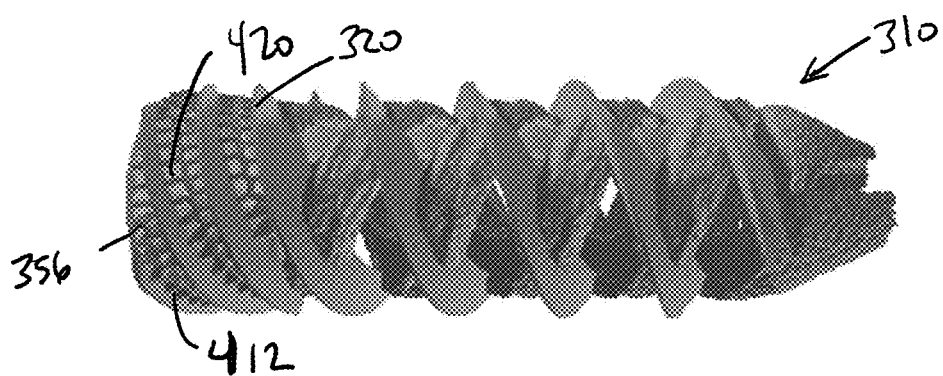
Figure 15:
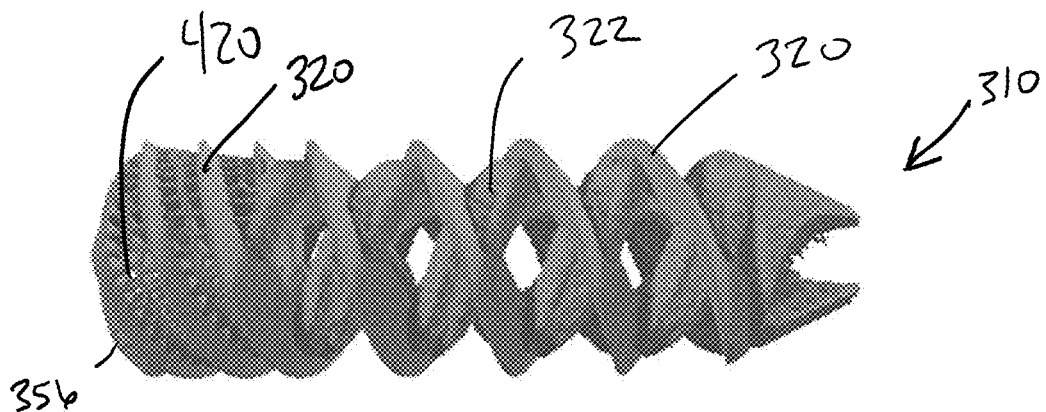
Figure 16:
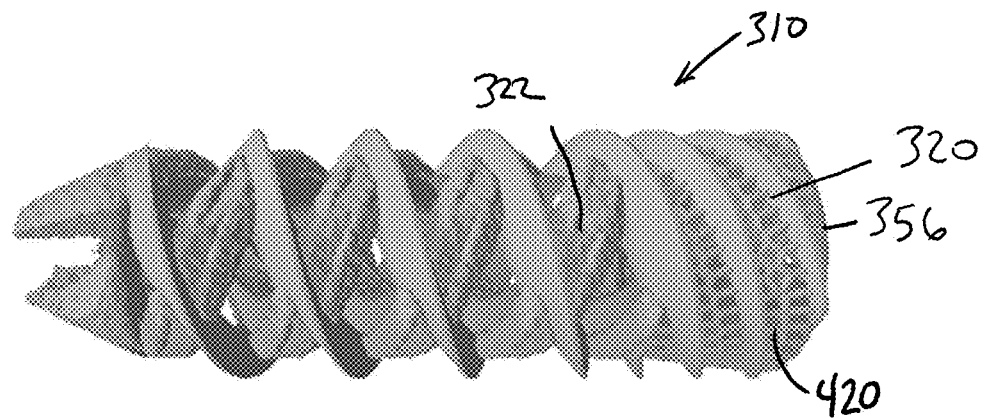

FIG. 13 shows an embodiment of bone screw 310 in which the inner diameter Dis of the threads 320 is smaller than the outer diameter Di of the inner framework helix 322. This creates an overlap 400 of volume between the two helices where they overlap as shown. This overlap 400 may vary in the percentage of overlap, but in one embodiment, the overlap 400 may be around 50%. In other embodiments, the overlap 400 may be between 45-55%, 40-60%, 25-75% or any other percentage of the thickness of the thread 320. In some embodiments, the dual helix bone screw 310 is additively manufactured in Grade V titanium using selective laser melting. This creates a roughened surface for increased bone purchase and on growth.

FIGS. 12-18 also show that the surface of the elements has a roughened surface containing rises and depressions arranged purposefully on the roughened surface 422 of the inner framework helix 322 and surface of the threads 320 are smoother than the surface of the inner framework helix 322. This allows a smooth surface to make cutting through the bone easier as the threads engage the bone surface, and also allows for better adhesion and ongrowth from the bone to the inner framework helix 322 and through holes 326. In another embodiment, the surface of the leading edge and cutting end 316 may include roughened surface 422.

From the foregoing, it will be seen that this invention is one well adapted to attain all the ends and objects herein-above set forth together with other advantages which are obvious, and which are inherent to the structure. It will be understood that certain features and sub combinations are of utility and may be employed without reference to other features and sub combinations. This is contemplated by and is within the scope of the claims. Since many possible embodiments of the invention may be made without departing from the scope thereof, it is also to be understood that all matters herein set forth or shown in the accompanying drawings are to be interpreted as illustrative and not limiting.

The constructions and methods described above and illustrated in the drawings are presented by way of example only and are not intended to limit the concepts and principles of the present invention. Thus, there has been shown and described several embodiments of a novel invention.

As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

We claim:

1. A bone screw comprising:
   a body having a diameter and a longitudinal axis in a direction perpendicular to the diameter;
   a leading end;
   a driven end, wherein the leading end and the driven end define a length of the body;
   at least one thread helix along a portion of the length of the body, the at least one thread helix being disposed at a first downward thread angle from the driven end and at a first direction of rotation about the longitudinal axis of said body; and
   at least one inner frame helix disposed at a second downward thread angle from the driven end and at a second direction of rotation about the longitudinal axis of said body,
   wherein the first downward thread angle and the second downward thread angle are equal.

2. The bone screw of claim 1, wherein the first and second direction of rotation are opposite.

3. The bone screw of claim 1, wherein the at least one thread helix and the at least one inner frame helix include a first thickness and a second thickness, respectively, and the first thickness and the second thickness are sized such that an outer diameter of the at least one inner frame helix is greater than an inner diameter of the at least one thread helix thus creating a thickness overlap of the first thickness and the second thickness.

4. The bone screw of claim 3, wherein the thickness overlap is 25-75% of the first thickness of the at least one thread helix.

5. The bone screw of claim 3, wherein the thickness overlap is about 50% of the first thickness of the at least one thread helix.

6. A surgical screw comprising:
   at least one helical thread arranged in one of a right hand helix and a left hand helix, said at least one helical thread having a first thickness partially defined by an inner diameter;
   at least one inner framework helix arranged in the other of the right hand helix and the left hand helix, said at least one inner framework helix having a second thickness partially defined by an outer diameter; and
   wherein the inner diameter of the at least one helical thread is smaller than the outer diameter of the at least one inner framework helix, thus creating an overlap of the first thickness and the second thickness.

7. The surgical screw of claim 6 wherein the overlap is 25-75% of the first thickness of the at least one helical thread.

8. The surgical screw of claim 6, wherein the thickness overlap is about 50% of the first thickness of the at least one helical thread.

* * * * *